United States Patent [19]

Staff et al.

[11] Patent Number: 5,619,333
[45] Date of Patent: Apr. 8, 1997

[54] FLOW CONTAMINATION MONITOR

[75] Inventors: Paul E. Staff; David Button; John D. Pratt, all of Suffolk; Dominic P. E. Barnard, Oxon, all of England

[73] Assignee: UCC Corporation of Engadinstrasse, Switzerland

[21] Appl. No.: 407,060

[22] Filed: Mar. 17, 1995

Related U.S. Application Data

[63] Continuation of Ser. No. 849,057, filed as PCT/GB93/01882 Dec. 4, 1990, abandoned.

[30] Foreign Application Priority Data

Dec. 4, 1989 [GB] United Kingdom ............... 8927371

[51] Int. Cl.$^6$ .............. G01N 21/00; G01N 15/02
[52] U.S. Cl. .............. 356/436; 356/335; 73/61.69; 377/11
[58] Field of Search .............. 356/436, 432, 356/433, 435, 440, 441, 442, 243, 335–343, 244, 246; 250/573, 576, 577, 222.2; 73/61.69, 61.73; 377/10, 11

[56] References Cited

U.S. PATENT DOCUMENTS

| 3,177,706 | 4/1965 | Shuman et al. | |
|---|---|---|---|
| 3,591,290 | 7/1971 | Baker et al. | 356/436 |
| 3,627,424 | 12/1971 | Dorman et al. | 356/338 |
| 3,785,734 | 1/1974 | Walters et al. | 356/436 |
| 3,864,044 | 2/1975 | Lyshkow | 356/436 |
| 3,876,307 | 4/1975 | Skala | 356/434 |
| 4,126,038 | 11/1978 | Bartlett et al. | 73/118 |
| 4,181,009 | 1/1980 | Williamson | |
| 4,260,258 | 4/1981 | Rose et al. | 356/246 |
| 4,434,647 | 3/1984 | Whitcomb et al. | 356/243 |
| 4,663,966 | 5/1987 | Fisher et al. | 73/61.73 |
| 4,685,066 | 8/1987 | Hafele et al. | 73/61.73 |
| 4,950,610 | 8/1990 | Tittle | 356/435 |

FOREIGN PATENT DOCUMENTS

| 1375280 | 9/1964 | France. |
| 1278784 | 6/1972 | United Kingdom. |

*Primary Examiner*—Hoa Q. Pham
*Attorney, Agent, or Firm*—Andrus, Sceales, Starke & Sawall

[57] ABSTRACT

The invention relates to a portable on-line fluid contamination monitor. An inlet and an outlet are provided for connecting the monitor to a fluid control circuit and a measuring device is included for withdrawing fluid from the circuit. An optical sensor assembly is used to view fluid withdrawn from the circuit and to determine the level of contamination by observation of the particles therein, the optical sensor assembly viewing the fluid through a window by means of a light source disposed to project light through the window and the fluid. A light sensor disposed on the opposite side of the window from the light source is arranged to detect particles in the fluid passing across the window by sensing the degree of light obscuration caused by particles in the fluid.

19 Claims, 8 Drawing Sheets

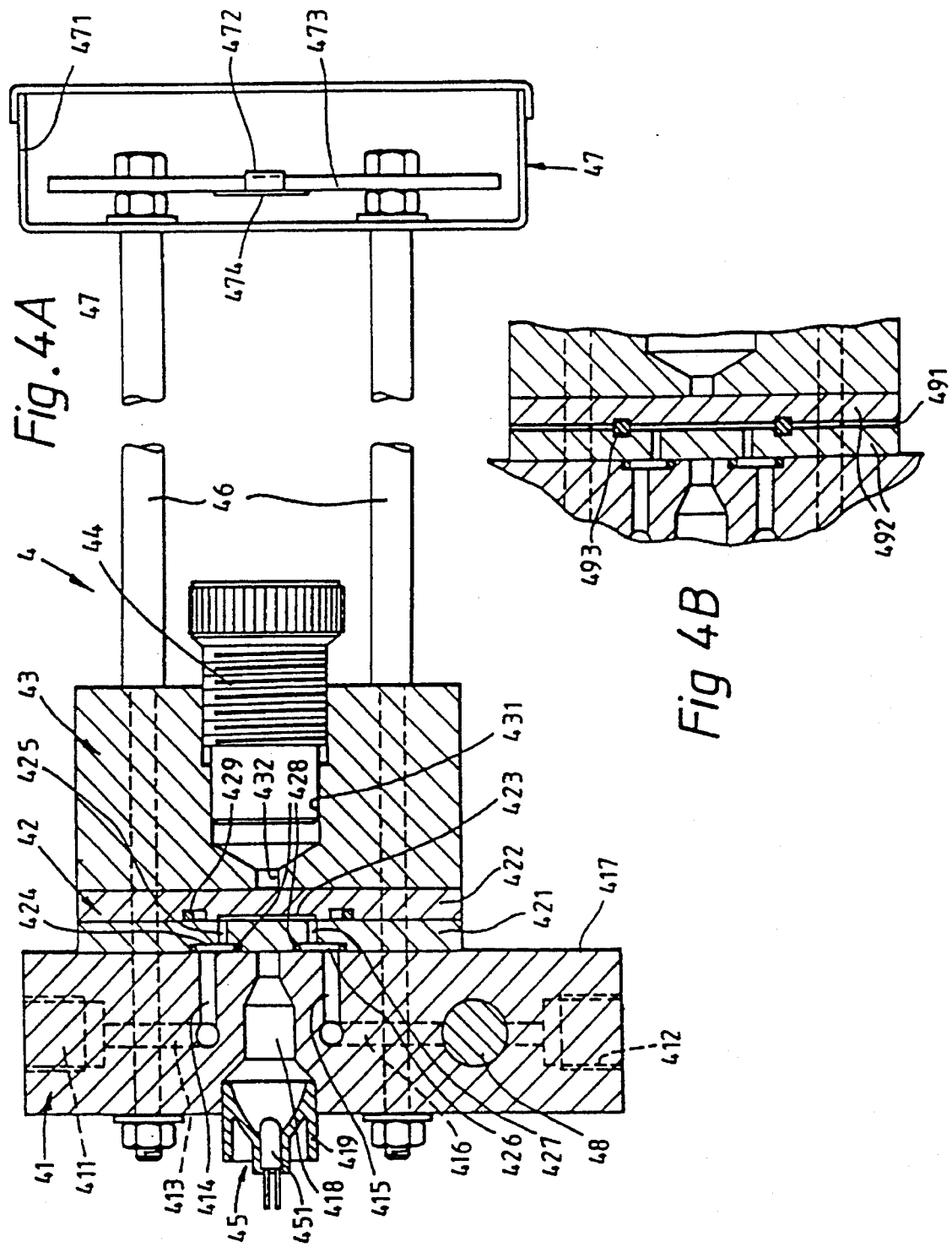

FLOW CONTAMINATION MONITOR

The present application is a continuation application of U.S. patent application, Ser. No. 07/849,057, filed as PCT/GB93/01882 Dec. 4, 1990, and now abandoned.

The present invention relates to the monitoring of particulate contamination of fluids and, more particularly, to the contamination of fluids such as hydraulic fluid.

The monitoring of contamination levels in hydraulic fluid that is used in equipment such as earth-moving equipment, machine-tools and the like is important in order to ensure that the hydraulic fluid is changed before contamination reaches a level at which damage to or malfunction of the hydraulic equipment may occur. Contamination of hydraulic fluid may arise from sand particles left over from the casting processes used for manufacturing flow control valves, hydraulic rams etc., from metal particles broken or worn away from the various hydraulic components and from particles of rubber breaking away from seals, hoses and the like. Particulate contamination can result in premature failure of component elements and the problem is sufficiently serious that an International standard (ISO 4406) has been established to enable contamination levels to be quantified, thus permitting hydraulic component manufacturers to specify permissable system cleanliness levels.

Conventionally, samples of hydraulic fluid are extracted from systems through suitable bleed points, collected in "clean" containers and taken away to a laboratory for analysis in order to determine contamination levels.

However, the measurement of contamination levels in this way has serious drawbacks. Firstly, the need to withdraw fluid from the hydraulic system means that bleed-off points need to be carefully positioned to ensure that the fluid which is analysed is a realistic sample of the fluid in the system. This may be difficult to achieve, particularly if fluid can only be bled off when the hydraulic fluid is not under pressure. Secondly, the requirement to remove the fluid for laboratory analysis means that results are not immediately available so that continued working of equipment whilst laboratory analysis is taking place may involve protracted operation of the hydraulic circuit whilst serious contamination levels are present, resulting in damage to hydraulic components. In other words, the results are not available immediately for use. Thirdly, absolute cleanliness of collecting vessels, pipes, etc. is essential in order to ensure that the samples taken contain only system contaminants.

Systems are known which enable "on site" determination of contaminants, but these systems involve passing fluid through a membrane through which the liquid may pass but the contaminants may not. The membrane is removed after a given quantity of fluid has passed through it or after a given time has lapsed and the membrane, with the contaminants held thereon, is then compared with a standard set of slides indicating degrees of contamination, comparison being made with the human eye to establish which of the standard slides most closely resembles that of the removed membrane. Clearly, such systems are open to considerable inaccuracy, are time consuming and, of course, are not automatic.

Other known methods using on-line electronic particle counters are available, but are not normally sufficiently portable or robust for field use.

There is a need therefore to provide a more practical method of field monitoring fluid contamination and according to the present invention there is provided an on-line fluid contamination monitor comprising means for connecting the monitor to a fluid circuit; means for withdrawing fluid from the circuit; and optical means for viewing the fluid withdrawn from the circuit and determining the level of contamination by observation of the particles therein, the optical means viewing the fluid through a window by means of a light source disposed to project light through the window and the fluid, and having a light sensor disposed on the opposite side of the window from the light source and arranged to detect particles in the fluid passing across the window by sensing the duration and extent of light obscuration caused by particles in the fluid.

The light sensor is preferably a photodiode which is partially masked by a slit in order that only a selected portion of the light which is passed through the fluid and window, and focused on to the photodiode by a suitable lens, impinges on the photodiode. The size of the slit is determined by the minimum size of particle required to be measured and the sensitivity of the electrical system.

Preferably, the duration and extent of light obscuration caused by particles in the fluid are determined by measuring both the length and amplitude of the sensor signal. Withdrawal of fluid at a predetermined rate for a predetermined volume is preferred in order that the detection of particles by sensing duration and extent of obscuration can accurately be converted to a measurement of particle size and concentration. However, if flow rate is accurately measured then variable flow rates may be accommodated.

Preferably, fluid is withdrawn at a predetermined rate by withdrawing a predetermined volume of fluid in a predetermined time and this may be achieved by means of a cylinder and piston assembly arranged so that the piston is motor driven over a predetermined distance, such as the length of the cylinder.

Advantageously, and in order to reduce the time taken to carry out a contamination test, such a piston/cylinder and motor drive unit will comprise a double acting piston whereby fluid to be monitored can be drawn into and out of each end of the associated cylinder, appropriate valving being provided as required.

In particular, but not exclusively, the system may be provided with two ports for attachment to a hydraulic circuit, the ports being connected to the corresponding ports of, typically, a UCC "System 20" pressure sensor (see EP-B-0124218 and EP-B-0119038) and providing a bypass path around the sensor, fluid being taken from the bypass path, passing through the optical viewing means, through a directional valve, to the cylinder/piston assembly, back through the directional valve and then back via the bypass path and into the downstream side of the "System 20" sensor. By this means, differential pressure across the monitor can be arranged to be very low and fluid can be passed back into the hydraulic circuit after having been used for contamination monitoring. When the next contamination test is carried out, movement of the piston in the opposite direction to that of the previous test and corresponding changing over of the directional valve can be used to draw fluid through the optical sensor.

In order to achieve high definition at the optical window, the optical viewing means may comprise a flow channel defined between a pair of transparent plates, the window being defined by a narrow channel formed in the plates or by a slit in an opaque foil disposed between the plates.

Appropriate magnification of the image obscuring light passing from the light source, through the window and through the fluid, can be achieved by means of a suitable lens in order to produce an enlarged image on the slit disposed in front of the photodiode used as a light sensor. Alternatively, the photodiode could be replaced with an array of diodes, with a charged coupled device (CCD) or other similar device.

One particular advantage of the system of the invention is that the tests can be carried out without environmental contact, thus increasing accuracy by avoiding contamination by contaminants from outside the hydraulic system under examination.

One example of a contamination monitor according to the present invention will now be described with reference to the accompanying drawings in which:

FIG. 4A is a part sectional view of the optical sensor assembly;

FIG. 4B shows a modification to the optical assembly;

Figure 5A:
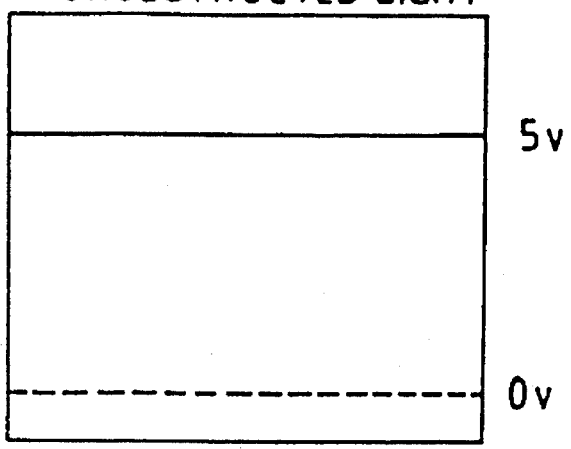
FIG. 5A shows a waveform plot of photodiode output when there is no light obscuration.
Figure 5B:
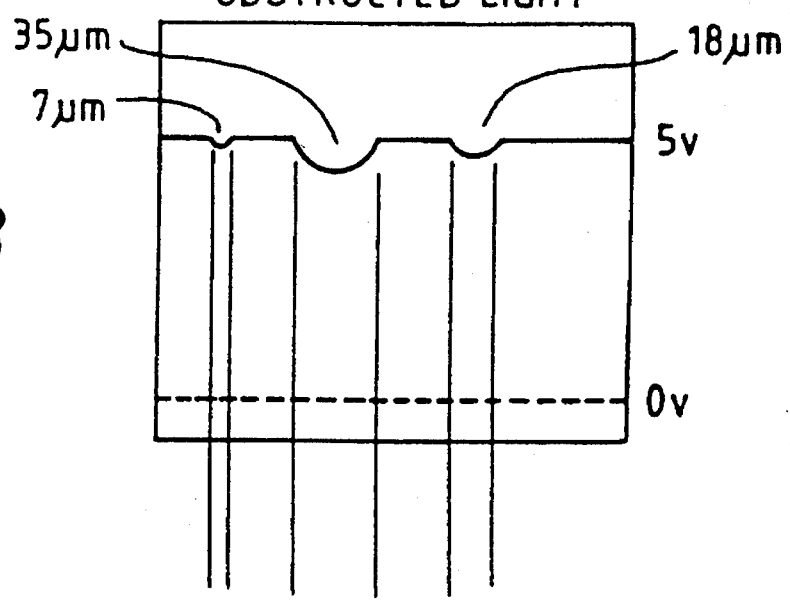
FIG. 5B is a similar plot showing the output due to various sized particles being detected.
Figure 5C:
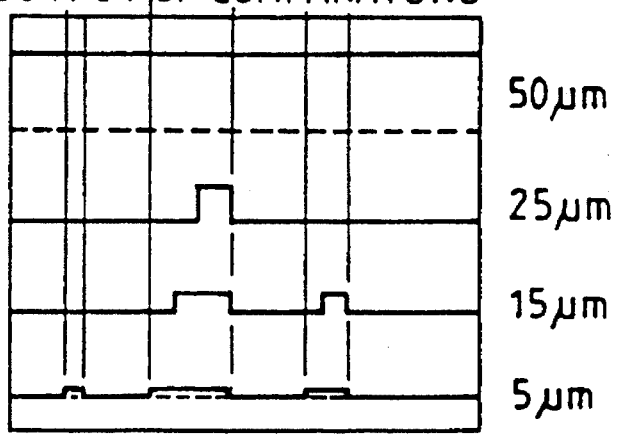
Figure 6:
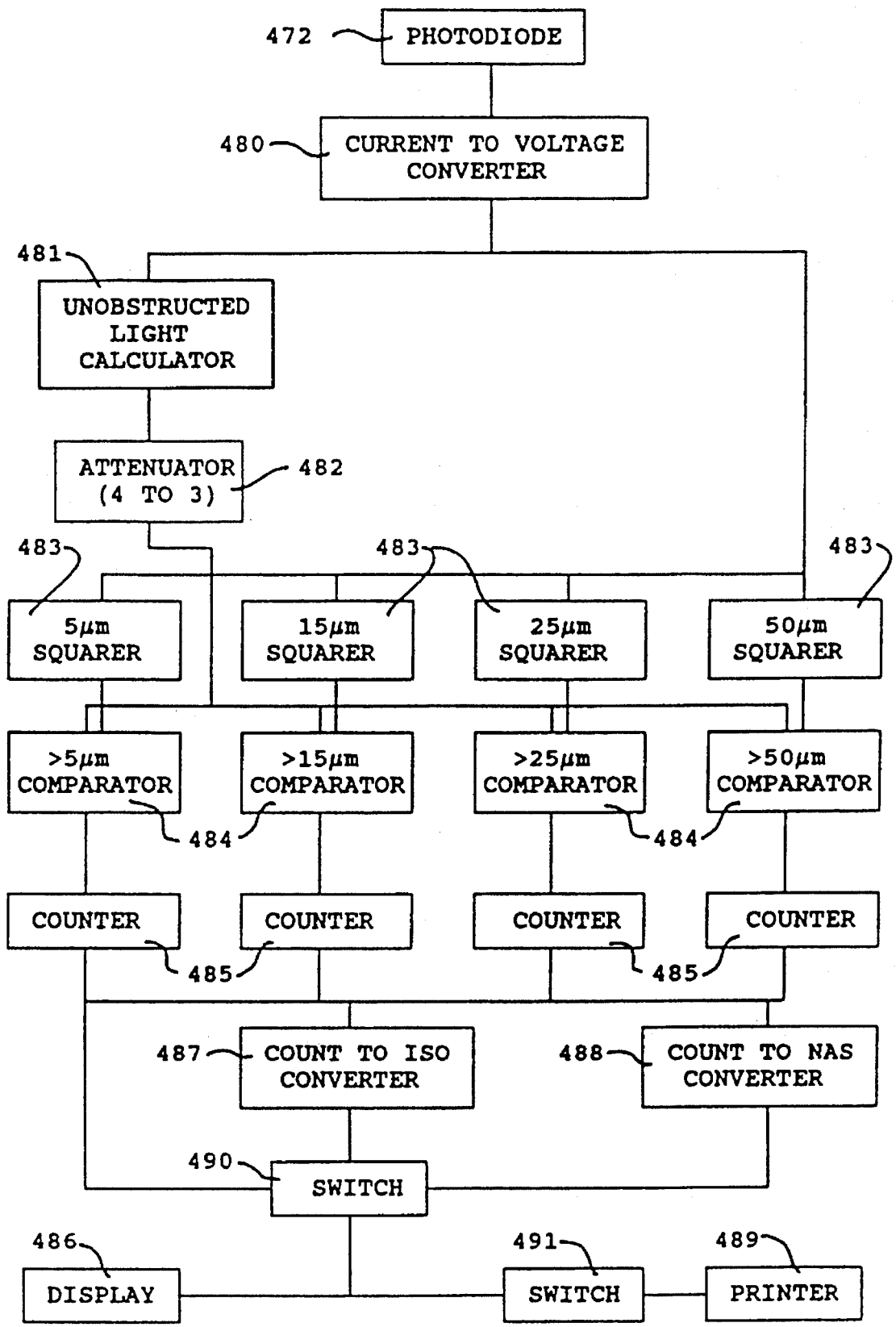

FIG. 5C indicates the output signals of four comparators used to produce counter pulses;

FIG. 6 is a schematic block diagram of the contamination level calculating electronics.

Figure 7:
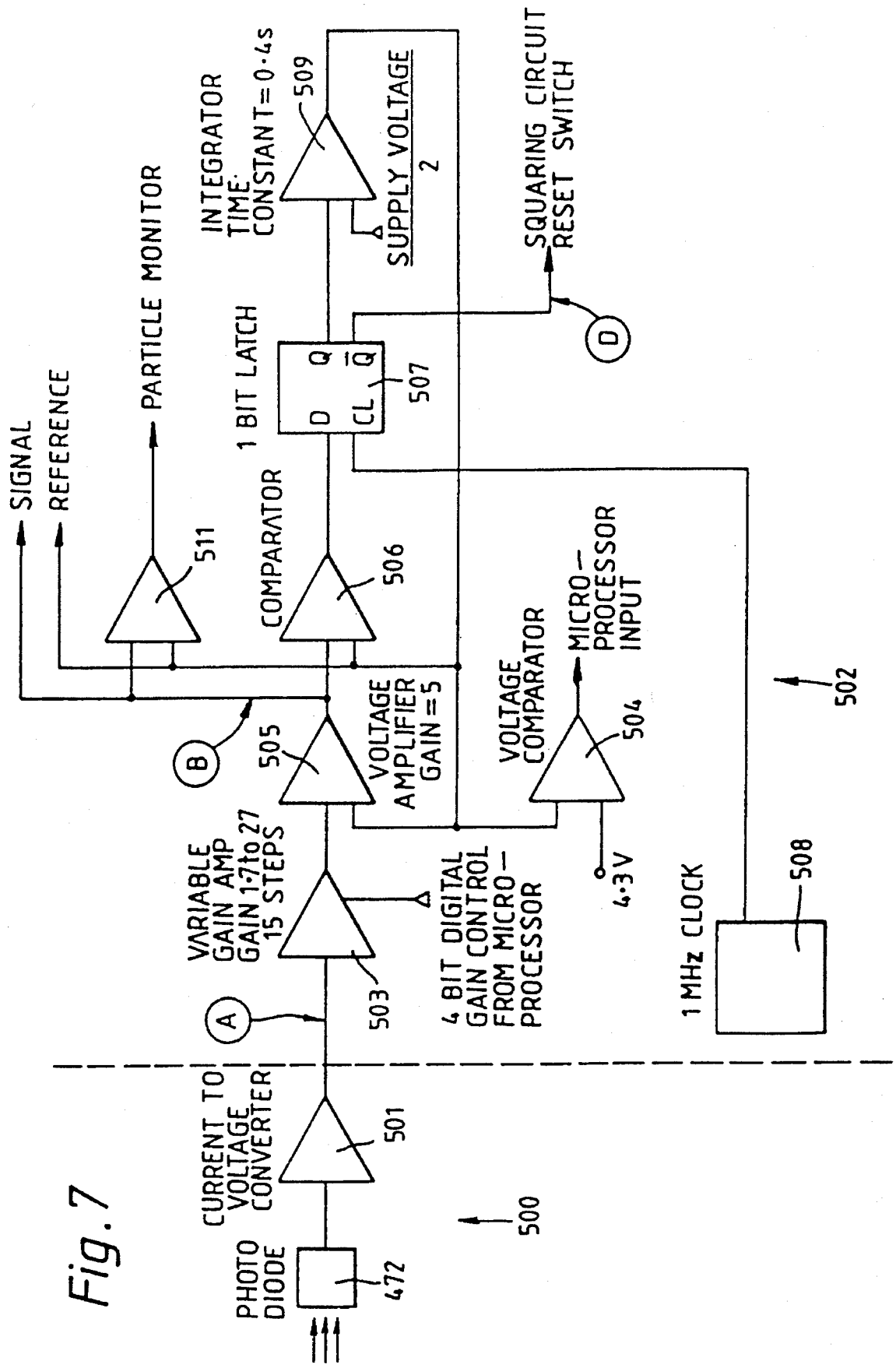
Figure 8:
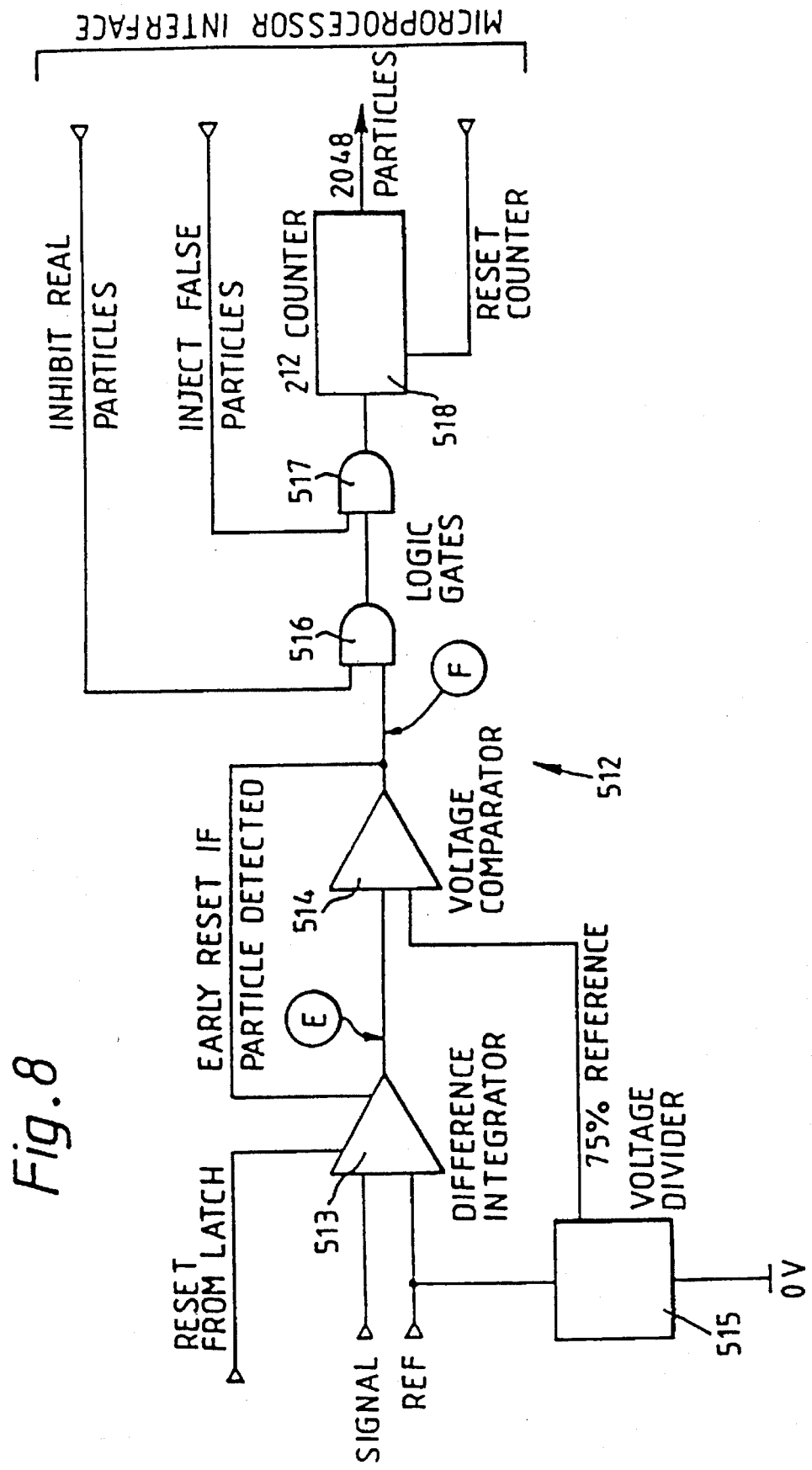

FIGS. 7 and 8 are simplified circuit diagrams of the electronic components employed in calculating the contamination level; and FIGS. 9A to 9F indicate various signals at points in FIGS. 7 and 8.

Figure 1:
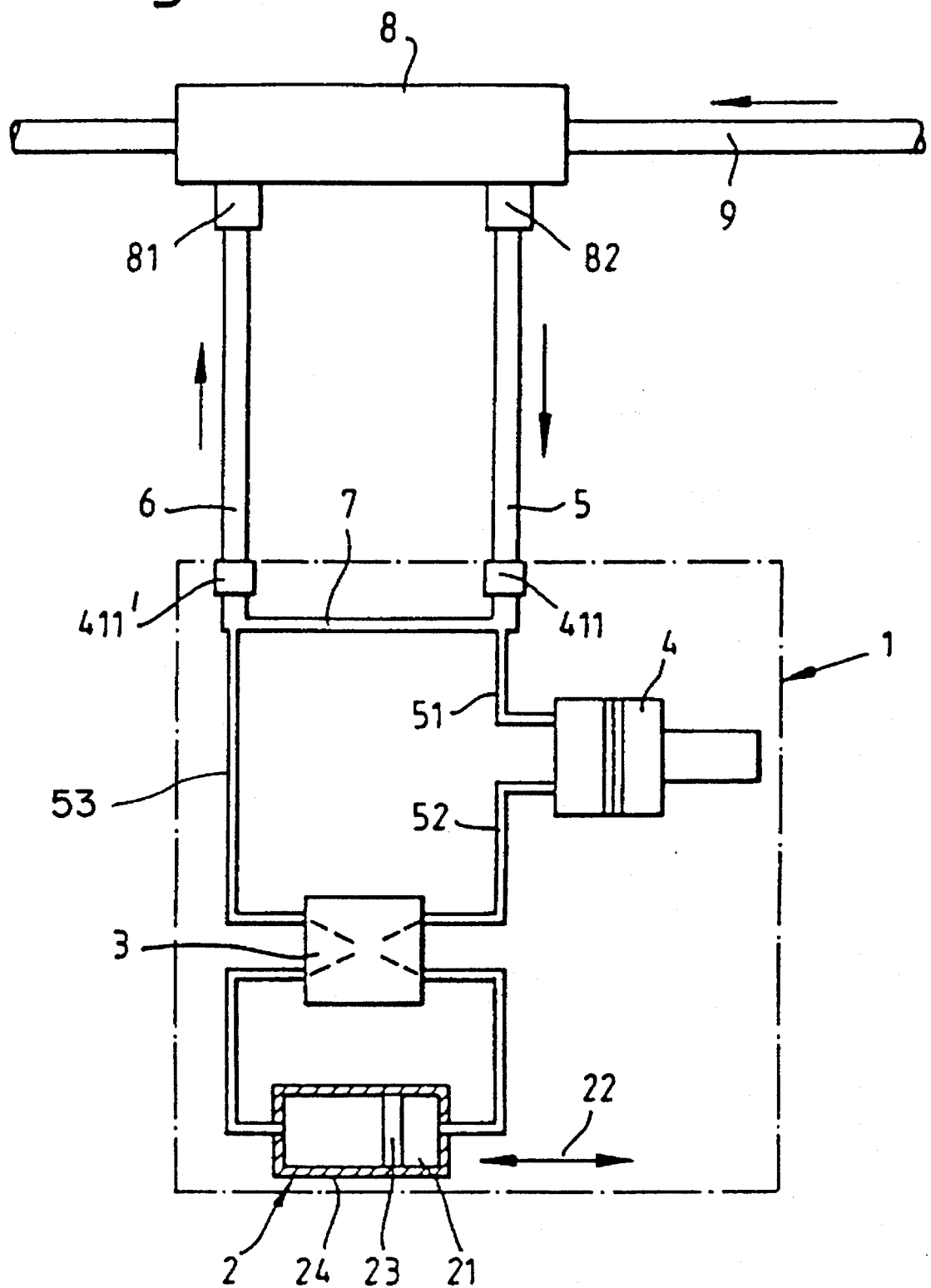
FIG. 1 is a schematic circuit diagram of the monitor attached to a hydraulic circuit.

FIG. 1 shows in schematic form a hydraulic circuit containing a monitor according to the invention. The monitor 1 includes the various components shown within the dotted line in FIG. 1 and, in particular, includes a motor driven measuring device 2, a directional valve 3 and an optical sensor assembly 4. The various components of the monitor 1 are connected by conduits as shown and as will be described in more detail later. The monitor is shown connected at ports 411, 411' to conduits 5,6 which, together with a bypass duct 7 in the monitor 1, pass fluid around a pressure sensing valve assembly 8 connected in a hydraulic flow line 9. The sensor assembly 8 is preferably a UCC "System 20" valve assembly of the type conventionally used in a condition monitoring system for measuring flow rate, working pressure or temperature. Such a sensor is often permanently installed in a fluid line to provide an intrusion point to probe the hydraulic system.

The sensor includes a variable area orifice with a pair of sensing ports 81, 82 to which, in the case of the present invention, the bypass duct 7 is connected. In use flow is directed, under action of pressure across the sensor 8, from the sensor 8, through the conduit 5 into the port 411 and from there into the bypass duct 7, to the outlet port 411', into the conduit 6 and back to the low pressure side of the sensor and thus return to the hydraulic line 9. Fluid is also bled through line 51 under the action of the measuring device 2 (which will be described in more detail in relation to FIGS. 2 and 3), the hydraulic fluid flowing through the optical assembly 4, the directional valve 3 and into the measuring device 2. The measuring device 2 includes a double-acting motor driven piston 23 and cylinder assembly 21 into one end of which fluid is first drawn, the fluid from the other end passing at the same time through the other line of the directional valve 3 and back through the other port 411' and into the conduit 6, and hence to the hydraulic line 9. The motor drive 22 of the measuring device 2 causes the piston 23 to move along the cylinder 24 until a required volume of fluid has been displaced, thus ensuring that a given volume of fluid passes through the optical sensor assembly 4. After the completion of one test the directional valve is reversed by the operator and when the motor is next started for movement of the piston in the reverse direction, hydraulic fluid in the cylinder is returned to the hydraulic line 9 as fresh fluid is drawn through the optical sensor assembly for examination.

A particular advantage of the arrangement shown is that system pressure is unimportant to the operation since it acts with controlled low differential pressure on both sides of the piston. Viscosity is also unimportant since the flow rate is determined by the positive displacement of the piston 23 and the cylinder 24.

Figure 2:
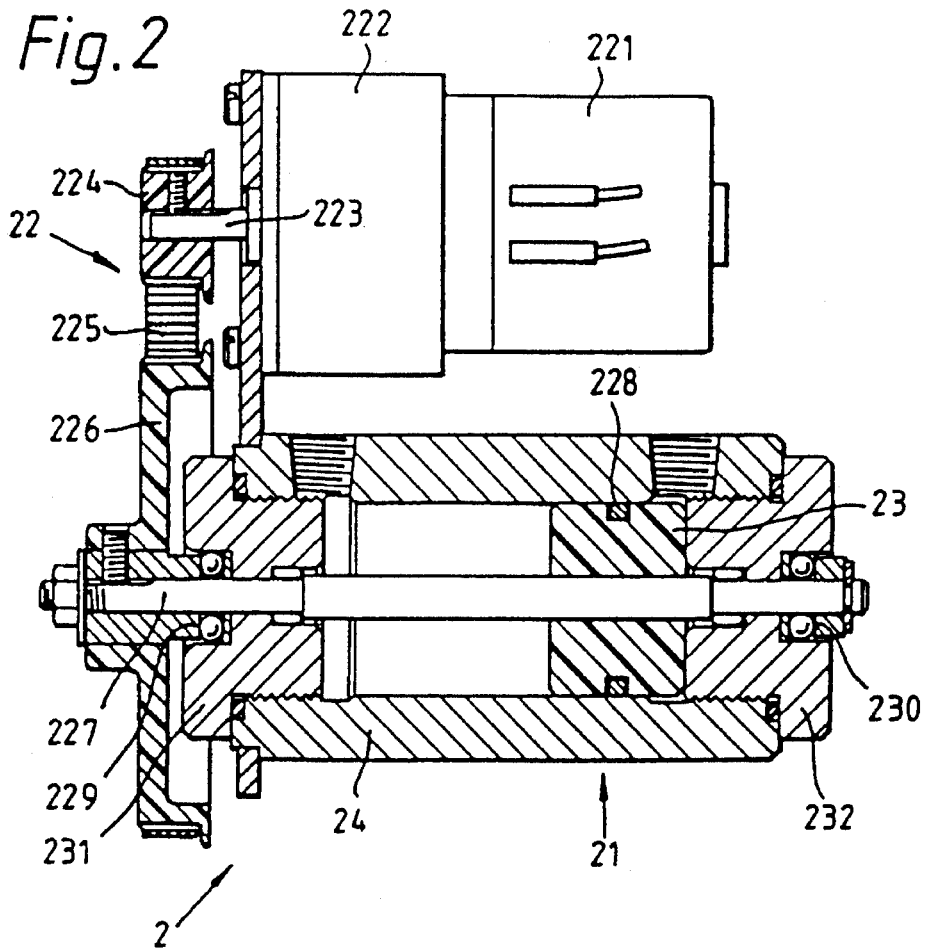
FIG. 2 is a part sectional view of a motorised measuring device of the monitor.
Figure 3:
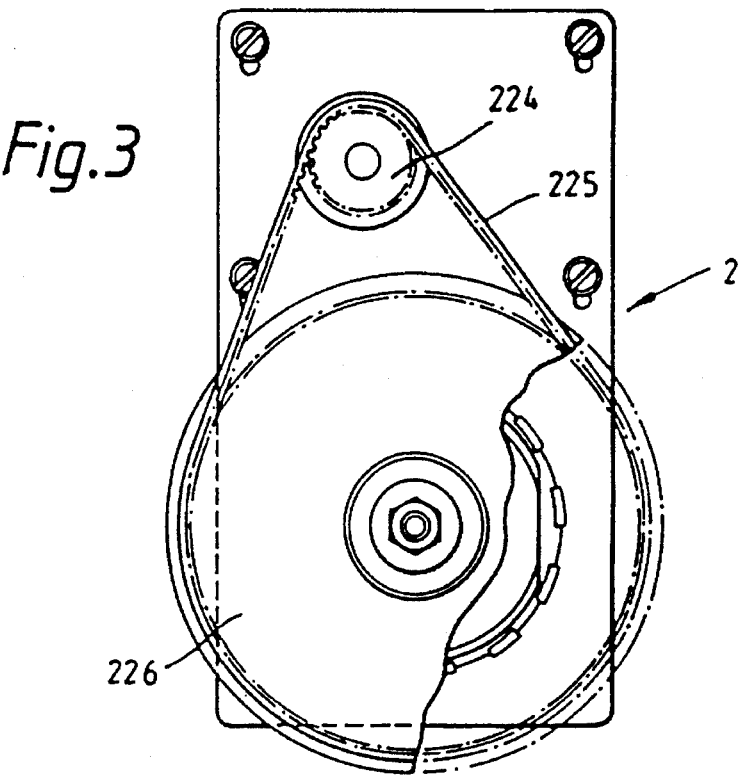
FIG. 3 is an end view of the motorised measuring device.

The measuring device is shown in more detail in FIGS. 2 and 3. The motor drive 22 has a motor 221 which may include an integral gearbox 222 to drive an output spindle 223 at say 60 rpm. The motor spindle 223 mounts a toothed sprocket 224 which, through a toothed belt 225 drives a larger toothed sprocket 226. The sprocket 226 drives a threaded spindle 227 which passes axially through the cylinder 24 and which, in turn, causes the piston 23 to move along the length of the cylinder when the motor 221 is in operation. The low rotational speed of the piston spindle 227 enables the piston 23 to move slowly from one end of the cylinder to the other and avoids the need for restraint on rotation of the piston 23 other than that caused by the pressure of an O-ring seal 228. The piston spindle 227 is located by end bearings 229, 230 and end plates 231, 232 of the cylinder 24.

The directional valve 3 is of conventional construction and is manually operated in this example and includes micro-switches (not shown) to provide signals to the system electronics to indicate correctness of operation.

The optical sensor assembly 4 (see FIG. 4A) has a main support block 41 with inlet 411 and outlet 412 ports which connect with hydraulic input 51 and output 52 lines (see FIG. 1). Internally of the block 41 passages 413–416 connect the inlet 411 and outlet 412 with a window assembly 42 which comprises a pair of transparent perspex windows 421,422 which define a narrow passageway 423 (in the example 0.6 mm width by 0.2 mm thickness) through which hydraulic fluid is passed for examination. Passageways 424–427 in the perspex window 421 enable the input and output of hydraulic fluid to the recess 423, O-rings 428,429 sealing the window 421 against the face 417 of the block 41 and the window 422 against the window 421 respectively. Against the side of the window assembly 42 opposite the block 41 a lens mount 43 is provided, the lens mount having a main bore 431 and a narrow counter bore 432 which is aligned with the window recess 423, the lens assembly 44 being adjustably mounted in the bore 431.

The block 41 also includes a central passageway 418 which is aligned with the recess 423 in the window assembly 42 and a light fitting 45 which includes a bulb 451 is located in the entrance 419 to the passageway 418. Four mounting rods 46 which are threaded at both ends are used to retain the assembly of the block 41, window assembly 42 and lens mount 43 and also, at their opposite end, mount a photodiode assembly 47 which includes a housing 471, in which are mounted a photodiode 472 on a support 473. A slit 474 (of dimensions 25 μm×2 mm) onto which light from the bulb 451 is focused, having passed through the window assembly 42, by the lens assembly 44, is disposed directly over the face of the photodiode 472. The slit is orientated with its long dimension lying at 90° to the direction of fluid flow through the passageway 423.

An alternative construction has a foil mask 491 located between a pair of perspex windows 492 (as shown in FIG. 4B) as an alternative to window assembly 42 shown in FIG. 4A. A modified seal structure 493 is used.

The spindle 48 of the directional valve 3 is located in the flow line 416 to the outlet 412 of the block 41.

In use, hydraulic fluid passing through the optical sensor assembly 4 is monitored for contamination by sensing the duration and extent of light obscuration of the photodiode 472 caused by particles passing through the recess 423. The particle density of even the most heavily contaminated hydraulic fluid, and the size of the recess 423, make it highly unlikely that the images of two contaminating particles can pass over the optical slit together, so that any reduction in photodiode output can be interpreted as being caused by the shadow of a single particle and its size will determine the amount of signal reduction. The recess 423 provides, in effect, a gate through which hydraulic fluid can be viewed.

In operation fluid flows through the narrow passageway or recess 423 in the window, which is illuminated by the high intensity lamp. The emerging light is focused by the lens 44 so that an image of contamination particles is projected onto the slit 474 and the photodiode 472. When a particle obscures some of the light falling on the slit, the electrical output of the diode is reduced in relation to the size of the particle as is described below.

In use, the light that has passed through the sample is focused on to the slit 474 and an image of any particles in the fluid is formed on the surface of the slit. A transverse section of the image equivalent to a strip of oil 5 μm wide and 400 μm long passes through the slit on to the photodiode. The magnitude of the current generated, as a result, by the photodiode is proportional to the light that would pass through clean oil less any light obstructed by contaminant particles.

FIG. 6 is a schematic block diagram of the calculation electronics which has been prepared to simplify the description, the precise details of the circuitry being shown in FIGS. 7 and 8. The photodiode current output is linearly converted to a 5 volt signal in a current to voltage converter 480 (see FIG. 6).

In order to be able to calculate particle sizes it is necessary to have available at all times a reference voltage that is proportional to the unobstructed light. This voltage is seen in FIG. 5A. This voltage is generated in unobstructed light calculator 481. To calculate the areas of the particles passing through the window, the output voltage of the current to voltage converter 480 (see FIG. 5B) and the unobstructed light calculator 481 are fed to four squarers 483, each of which has a different sensitivity. For a given particle signal into the squarers, the outputs are in the ratios shown below:

| | | |
|---|---|---|
| 5 μm squarer | 1.00000 | (1 divided by 1 squared) |
| 15 μm squarer | 0.11111 | (1 divided by 3 squared) |
| 25 μm squarer | 0.04000 | (1 divided by 5 squared) |
| 50 μm squarer | 0.00100 | (1 divided by 25 squared) |

Figure 9A:
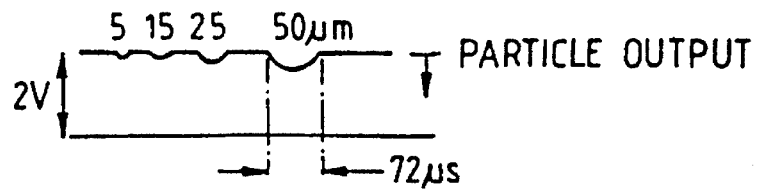
Figure 9B:
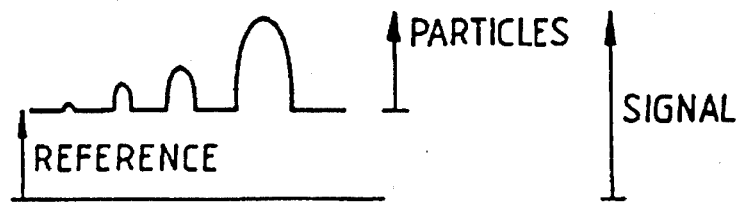
Figure 9C:
Figure 9D:
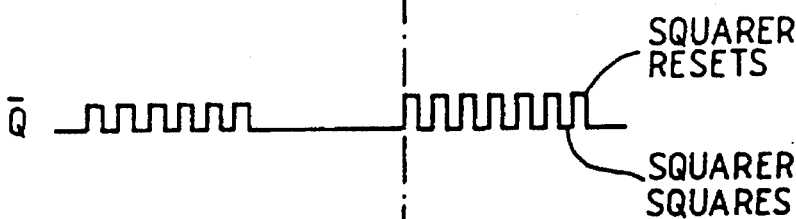
Figure 9E:
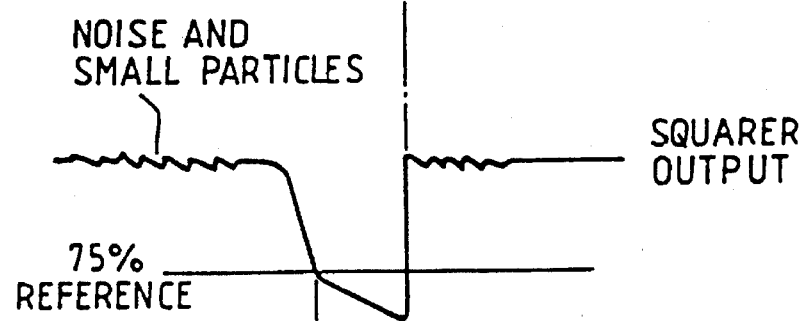
Figure 9F:
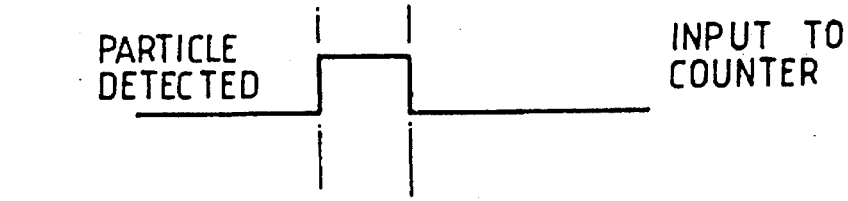

The output of each squarer is as shown in FIG. 9E. The same comparator level can then be used in each comparator 484, each of which receives a reference signal attenuated to 75% of the voltage from the unobstructed light calculator.

Comparators 484 compare the squarer outputs with the reference voltage and whenever the squarer voltage is caused to drop below 75% of the unobstructed light voltage (by a particle), the respective comparator outputs a counter pulse (see FIG. 5C) to a corresponding counter 485.

The counters are reset at the start of each test and the values of the counters 485 may be fed directly to a display 486 or via either an ISO code converter 487 or an NAS code converter 488 depending on the setting of a switch 490. The output to the display 486 may additionally be fed to a printer 489 when desired, as indicated by switch 491.

The signal processor electronics is provided on three PCBs mounted with the optical system in a screened box within the contamination monitor.

The first board 500 (see FIG. 7) mounts the photo diode 472. The light that has passed through the oil cell and the slit is absorbed by the photo diode 472 which converts the energy into a current of about 1 μA. An operational amplifier 501 used in "current to voltage converter" mode turns the current into a 1 volt signal. The particles appear as short term reductions in this voltage at 'A' in FIG. 7 (see FIG. 9A). The magnitude and duration of the reduction in output voltage due to a particle isproportional to its size. The actual reduction that occurs in practice is less than that predicted from theory because of three factors: (i) the optical system does not produce a completely black image of the particle; (ii) for particles below 8 μm the limited resolving power of the lens causes a reduction in the contrast ratio of the image; (iii) the size of the slit becomes significant (5 μm) with small particles which do not obstruct the light in proportion to their diameter.

The frequency response of the operational amplifier 501 is controlled to be level from DC to about 100 kHz. The output then falls rapidly to a low level. The phase shift in the operational amplifier is such that a 10% overshoot occurs at the end of each transient. The purpose of the enhanced response is to compensate partially for the lack of resolving power in the lens. Also the beginning and ends of particles become exaggerated which helps the determination of when particles start and finish. This is one of the prime purposes of the signal processor. The voltage signal from the first board 500 (from the operational amplifier) is passed to a second board 502 (see FIG. 7).

Since the amplitude of the signal from the diode board 500 cannot be guaranteed (variations in the brightness of the lamp and the sensitivity of the photocell account for most of the tolerance) the first stage of the second board is an amplifier 503 with microprocessor controlled gain. The gain may adjusted from 1.7 to 27 in 15 more or less equal steps. The largest step is 33%. At the beginning of each test just after the lamp 451 comes on and the motor drive 22 has been running for a few seconds the microprocessor increases the amplifier gain one step at a time. It starts at the lowest setting and increases the gain until the output of a comparator 504 that compares the (reference) output of a later stage of the processor with 4.3 volts has changed state. This means that the signal voltage at this point is always adjusted to be between 4.3 V and 5.7 V.

At this point it should be understood that to detect the start, size and end of a particle the obstructed signal from the photodiode is compared with the signal that would have existed if the light had not been obstructed. It is thus necessary to generate a voltage that represents the unobstructed light. To do this certain assumptions must be made about the nature of this signal. Firstly, that the signal will not rise or fall at a rate of more than 1% in 10 ms and secondly that the light is not obstructed for more than a small part of the total time. For a homogeneous oil that does not have unmixed patches of water, carbon, dirt or oxidation or an excessive number of particles in it these assumptions are realistic.

The next stage is an amplifier 505 in which the particle part of the signal but not the unobstructed part of the signal, is amplified by 5.1 and inverted. An alternative way of looking at this is to say that the amplifier has a gain of 5.1 but the DC part of the signal, which would have become at least 23 V (4.3×5.1) is stripped off and replaced by a voltage equal to the unamplified voltage. It is actually replaced by the unobstructed voltage (or "reference"). The output at 'B' in FIG. 7 (see FIGS. 9B & 9C) of this stage 505 is fed directly to three points:

1. A comparator 506 where the signal is compared with the unobstructed voltage. This comparator has a balance control which is set during manufacture to minimize the offset. It should be realized that the signal contains a small amount of thermal noise from the first operational amplifier plus sub 5 μm particles which appear as noise. If when the signal is unobstructed the signal including the noise is the same value as the unobstructed voltage the output of the comparator will be a lot of high frequency random pulses the mark space ratio of which will be 1:1. The digital noise is fed into a flip-flop 507 which is clocked at 1 mHz by clock 508. The $\overline{Q}$ output of the flip flop at 'D' (see FIG. 9D) is a random series of 1 μs wide pulses. These pulses serve two purposes:
   a. The pulses are fed into an integrator 509 with a 0.4 s time constant. The output of the integrator will only cease to change when the digital noise at the input has a mark space ratio of exactly 1:1. To make sure this happens the output of the integrator 509 is fed back to the other input of the second stage amplifier 505 and the following comparator 506. This voltage sets itself to be equal to the DC component of the signal and is the unobstructed signal (on the circuit diagrams this is referred to as Reference).
   b. The pulses are also used to tell squaring circuits when to square and when not to square. When there are no particles that are distinguishable from the noise the pulses will be randomly 0's and 1's. The chance of the flip-flop state remaining as a 0 or a 1 for more than 2 or 3 μs at a time is very low. However when a particle is passing through the field of view the result will be very different. The signal will rapidly fall but the reference voltage will fall only very slowly. A difference will build up between them and the flip-flop 507 will give out only 0's at the $\overline{Q}$ output. When the particle has passed, the signal will rise to its original value and exceed or equal the value of the reference voltage. This will cause the flip-flop to produce a least one 1, and, when the feedback loop has stabilised, a string of 0's and 1's. Therefore any period during which the flip flop $\overline{Q}$ output is 0 there is a particle present and the squaring circuits should be working.
2. An instrumentation amplifier 511 of the particle counter.
3. The squaring circuits—these are on the third board 512. The third board 512 has four nearly identical particle counting channels (one of which is shown in FIG. 8). One channel is provided to count each of the particle sizes 5, 15, 25 and 50 μm.
Each channel consists of:
   a. A resettable integrator 513 to provide a squaring circuit. The signal minus the reference voltage—that is the particle signal is integrated whenever the output of the flip-flop is 0. The output of the integrator 513 at 'E' in FIG. 8 (see FIG. 9E) is proportional to the particle width in the slit (the drop in signal) multiplied by the particle length (the time the particle is visible in the slit and the signal is depressed). Every particle, including the noise, is integrated in all four channels. The outputs of the integrators are arranged to ramp negatively from 100% of the reference voltage until either the particle ends and the integrator resets or the integrator output exceeds 75% of the reference voltage, at which point the integrator resets even if the particle has not ended. This is achieved by means of a comparator 514 which receives a signal of 75% of the reference voltage from a voltage divider 515 and which outputs a signal at 'F' in FIG. 8 (see FIG. 9F) which is then fed to a counting system. This is to prevent the more sensitive channels being saturated by large particles after which they would take time to recover and possibly miss the next particle. The purpose of making the threshold, at which it is decided that a particular particle should be counted, a proportion of the reference voltage, is so that the calibration of the integrators remains constant When the light level fluctuates during a test. If this was not done the light level being received by the photo diode would need to be stabilised to ±0.05% to prevent errors in the calibration of the 5 μm channel.
   b. A gating and counting system. The output from the integrators can, with very dirty oil, be greater than 10,000 counts per second per channel. The microprocessor, which has other tasks to perform, cannot keep up with this rate. The cost of using a microprocessor compatible 4-channel counter system would be very high so a compromise has been reached. The pulses from the squaring circuit 513, each one representing a particle that crossed that channel's threshold, are fed into a 14 stage counter 518. The output state of 12th stage is read by the microprocessor. Every time it changes state the microprocessor adds 2048 particles to that channel's total. Changes of state will only occur at a maximum rate of 5 per second per channel. At the end of the test the microprocessor is faced with a problem. It has a number of blocks of 2048 particles that were seen but it does not know how many counts are still in the counter chain. The microprocessor solves this problem by, at the end of the test, first inhibiting (through a logic gate 516) any further counts that may come from the integrators and then injecting (through a further logic gate 517) its own false particle count pulses into the input of the counter. False particle counts are injected until the 12th stage changes state. The number of particles that were in the counter to start with is therefore 2048 minus the number put in by the microprocessor. This figure is added to the total already counted to give a complete number of particles seen in that test. The only differences between the four channels is the integrator time constant—the "threshold"—which is set by changing the time constant of the integrator. Each channel is permanently set to the same threshold voltage that has to be crossed before a particle is detected.

The time constants are adjustable and are set during manufacture using real oil samples:

| 5 μm channel | 0.1–1.1 μs |
| 15 μm channel | 1.5–9.0 μs |
| 25 μm channel | 3.3–19.8 μs |
| 50 μm channel | 15.0–90.0 μs |

The 5 μm channel has the output of the integrator brought out to the board connector to aid in setting the optical focus.

The system also includes suitable control electronics for the motor etc., all of which is considered to be well within the grasp of a competent electronics engineer and which is not therefore described in detail.

We claim:

1. An on-line fluid contamination monitor apparatus for determining the level at which a fluid flowing in a fluid circuit (8, 9) is contaminated by particles contained in the fluid, said apparatus comprising:

first conduit means (411, 7, 411') couplable to the fluid circuit, a portion of the fluid flowing in the fluid circuit (8, 9) being removed from the fluid circuit into said first conduit means and passed through said first conduit means;

second conduit means (51, 52, 53) in fluid communication with said first conduit means for providing a fluid flow path that is in parallel with at least a portion (7) of said first conduit means;

fluid displacement means (2, 3) coupled to said second conduit means, by means of which part of the fluid portion in the first conduit means is withdrawn from said first conduit means (411, 7, 411') and passed through said second conduit means (51, 52, 53) at a predetermined, controlled flow rate determined by said fluid displacement means, said fluid displacement means being directly coupled to said second conduit means downstream of the connection of the second conduit means to the first conduit means; and optical means (4) coupled to said second conduit means (51, 52) for viewing the fluid part passing through the second conduit means and determining the level of contamination by observation of the particles therein, the optical means viewing fluid through a window in said second conduit means by means of a light source disposed to project light through the window and the fluid, the optical means having a light sensor disposed on the opposite side of the window from the light source and arranged to detect particles in the fluid passing across the window at the predetermined controlled rate, and said optical means having means for determining the level at which the fluid is contaminated by particles by sensing the extent of light obscuration caused by particles in the fluid and by sensing the time durations that the particles moving at the predetermined, controlled rate obscure the light from the light source.

2. A monitor apparatus according to claim 1, wherein the light sensor is a photodiode which is partially masked by a slit in order that only a selected portion of the light which is passed through the fluid and window, and focused on to the photodiode by a suitable lens, impinges on the photodiode.

3. A monitor apparatus according to claim 2, wherein said monitor apparatus determines contamination of the fluid by particles having at least a predetermined minimum size and wherein the size of the slit is determined by the minimum size of particles that are required to be measured.

4. A monitor apparatus according to claim 1 wherein said optical means determines the duration and extent of light obscuration caused by particles in the fluid by measuring both the length and amplitude of a signal from the sensor.

5. A monitor apparatus according to claim 4, wherein said fluid displacement means is further defined as means by which a predetermined volume of fluid is withdrawn from said first conduit means and passed through said second conduit means at a predetermined flow rate in order that the detection of particles by sensing duration and extent of obscuration can accurately be converted to a measurement of particle size and concentration.

6. A monitor apparatus according to claim 4 wherein said fluid displacement means is further defined as means by which a predetermined volume of fluid is withdrawn from said second conduit means in a predetermined period of time.

7. A monitor apparatus according to claim 1 wherein said fluid displacement means is further defined as means by which a predetermined volume of fluid is withdrawn from said first conduit means and passed through said second conduit means at a predetermined flow rate in order that the detection of particles by sensing duration and extent of obscuration can accurately be converted to a measurement of particle size and concentration.

8. A monitor apparatus according to claim 7 further including means for accurately measuring the flow rate in said fluid flow conduit means to accommodate variable flow rates through the monitor.

9. A monitor apparatus according to claim 1 further including means for accurately measuring the flow rate in said second conduit means to accommodate variable flow rates through the monitor.

10. A monitor apparatus according to claim 1 wherein said fluid displacement means is further defined as means by which a predetermined volume of fluid is withdrawn from said second conduit means in a predetermined period of time.

11. A monitor apparatus according to claim 10, wherein fluid is withdrawn from said second conduit means by means of a cylinder and piston assembly arranged so that the piston is motor driven in the cylinder over a predetermined distance, said cylinder and piston assembly comprising said fluid displacement means.

12. A monitor apparatus according to claim 11, wherein the piston/cylinder assembly comprises a double acting piston, motor driven in a cylinder having two ends, whereby fluid can be drawn into and discharged out of each end of the cylinder through a directional valve.

13. A monitor apparatus according to claim 1 wherein said first conduit means includes an inlet port and an outlet port for attachment to said fluid circuit.

14. A monitor apparatus according to claim 13, wherein the inlet and outlet ports are connected to complementary ports of a pressure sensor in said fluid circuit.

15. A monitor apparatus according to claim 1, wherein, the optical means comprises a flow channel defined between a pair of transparent plates, the window being defined by a narrow channel formed by a slit in an opaque foil disposed between the plates.

16. A monitor apparatus according to claim 1 wherein said optical means includes a lens, and wherein light passing from the light source through the window and through the fluid is magnified by means of said lens.

17. A monitor apparatus according to claim 1 wherein the light sensor comprises an array of diodes, or a charged coupled device (CCD).

18. A monitor apparatus according to claim 1 wherein the fluid circuit contain an element across which a pressure drop occurs and wherein said first conduit means is couplable to the fluid circuit across the element so that the pressure drop across the element causes the fluid portion to flow through said first conduit means.

19. A monitor apparatus according to claim 1 wherein said optical means is located upstream of said fluid displacement means in said second conduit means.

* * * * *